(12) United States Patent
Unger et al.

(10) Patent No.: US 7,097,209 B2
(45) Date of Patent: Aug. 29, 2006

(54) STERILE COUPLING

(75) Inventors: Peter Unger, deceased, late of Stockholm (SE); by Birgitta Ekman Sparrman, legal representative, Stockholm (SE); Eric Westberg, Stockholm (SE)

(73) Assignee: Gambro Inc., Lakewood, CO (US)

( * ) Notice: Subject to any disclaimer, the term of this patent is extended or adjusted under 35 U.S.C. 154(b) by 127 days.

(21) Appl. No.: 10/240,507

(22) PCT Filed: Apr. 6, 2001

(86) PCT No.: PCT/SE01/00785

§ 371 (c)(1),
(2), (4) Date: Aug. 26, 2003

(87) PCT Pub. No.: WO01/76528

PCT Pub. Date: Oct. 18, 2001

(65) Prior Publication Data

US 2004/0034328 A1   Feb. 19, 2004

(30) Foreign Application Priority Data

Apr. 6, 2000   (SE) .................................. 0001278

(51) Int. Cl.
*F16L 35/00* (2006.01)
*A61B 19/00* (2006.01)

(52) U.S. Cl. .............................. 285/3; 285/4; 604/411; 604/905

(58) Field of Classification Search ................... 285/3, 285/4, 23; 604/905, 411
See application file for complete search history.

(56) References Cited

U.S. PATENT DOCUMENTS 2,667,184 A * 1/1954 Hailer et al. ................. 92/98 R
3,865,411 A * 2/1975 Rowe et al. ................. 285/363

(Continued)

FOREIGN PATENT DOCUMENTS

DE    4122476 A1 * 1/1993

*Primary Examiner*—James M. Hewitt
(74) *Attorney, Agent, or Firm*—John R. Merkling; Edna H. O'Connor; Laura B. Arciniegas

(57) ABSTRACT

Sterile coupling comprising a male and a female connector, each provided with a membrane device comprising a membrane surface covered with an adhesive at the exterior surface. When the connectors are brought into operation, the adhesive surface are contacted to form a bonded surface. Then, a hole is generated through the bonded surface and the sterile portions of the devices are brought into cooperations. The hole is formed by a rupture member arranged in one of the connectors. After rupturing, the membrane devices retract to a space formed between the cylindrical bodies of the connectors.

28 Claims, 8 Drawing Sheets

U.S. PATENT DOCUMENTS

| | | | | |
|---|---|---|---|---|
| 3,902,489 A * | 9/1975 | Carter | ..................... | 604/411 |
| 3,986,508 A * | 10/1976 | Barrington | ................. | 604/411 |
| 4,019,512 A * | 4/1977 | Tenczar | ..................... | 604/411 |
| 4,022,205 A * | 5/1977 | Tenczar | ..................... | 604/411 |
| 4,022,496 A * | 5/1977 | Crissy et al. | ................. | 285/3 |
| 4,030,494 A * | 6/1977 | Tenczar | ..................... | 604/411 |
| 4,418,945 A * | 12/1983 | Kellogg | ..................... | 285/70 |
| 4,630,630 A * | 12/1986 | Reynolds et al. | ........ | 137/68.23 |
| 4,828,557 A * | 5/1989 | Persidsky | ................... | 604/408 |
| 4,895,346 A * | 1/1990 | Steigerwald | ............ | 251/149.1 |
| 5,117,875 A * | 6/1992 | Marrucchi | ..................... | 141/1 |
| 5,269,771 A * | 12/1993 | Thomas et al. | ............. | 604/539 |
| 5,275,612 A * | 1/1994 | Bales, Jr. | ..................... | 606/205 |
| 5,492,147 A * | 2/1996 | Challender et al. | .... | 137/614.05 |
| 5,820,614 A * | 10/1998 | Erskine et al. | ............. | 604/533 |
| 6,234,538 B1 * | 5/2001 | Lauer | ......................... | 285/3 |
| 6,536,805 B1 * | 3/2003 | Matkovich | ..................... | 285/3 |
| 6,655,655 B1 * | 12/2003 | Matkovich et al. | ...... | 251/149.1 |
| 6,814,726 B1 * | 11/2004 | Lauer | ........................ | 604/535 |

\* cited by examiner

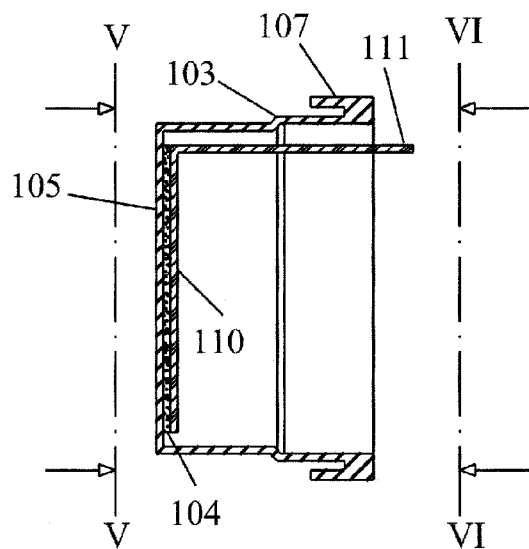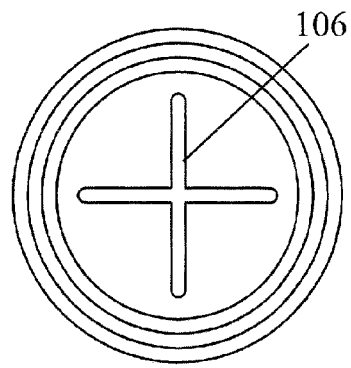
Figure 4
Figure 5
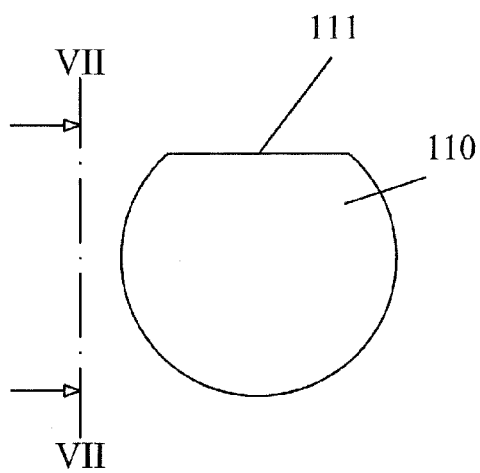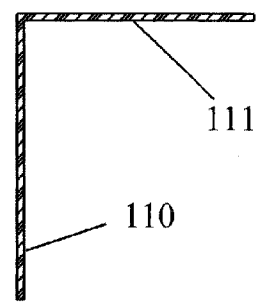
Figure 6
Figure 7

STERILE COUPLING

AREA OF INVENTION

The present invention relates to a sterile coupling. The coupling is intended to be used in medical applications, such as at the interconnection and mixture of two initially sterile fluids, or sterile connection of bags or devices to catheters entered into the body of a mammal. One specific field of use is the interconnection of bags comprising blood components which are to be subject to treatment, such as rejuvenation of an erythrocyte cell suspension, or virus elimination of a blood component or whole blood.

BACKGROUND ART

Transferring sterile material, such as biological liquids (blood, blood products, sterile liquids to be infused, medicines etc) between different containers, is subject to the categorical requirement that sterility has to be maintained during the whole transfer process.

Government requirements with respect to sterility can be summarized as follows: The sterile process shall be functionally equivalent to a "closed system" even though the process may be that of a "connected system". The present innovation addresses this challenge and its technical solutions have been chosen to achieve the sterile standard provided by a "closed system".

One application in which the invention may be used is in handling separated blood components. When the blood component has been separated, it is normally stored for a specific time period until it can be used for transfusion. The blood component must be preserved during this time period. After the storage and before transfusion, the blood component is often exposed to virus inactivation, in order to reduce or even eliminate the risk of virus infection. Such virus inactivation involves adding to the blood component a virus inactivation agent or liquid. Such addition of virus inactivation agent may take place before the storage or shortly before transfusion. In order to add such components, a sterile coupling is required.

Modern blood banks have a need for cost effective procedures and machines when preparing blood components in a safe and effective manner. One application is in the inactivation of virus and/or pathogens in cellular blood products such as red cell and platelet preparations. Currently, virus and pathogen inactivation entails adding photoactivated materials and exposure of the suspension to light of a suitable wave length, often ultra violet light for a given time interval. Future probable frequent use of these inactivation procedures point to the need of a sterile coupling which is simple, flexible and inexpensive.

A sterile coupling, which may be used in the above applications and similar applications is disclosed in DE 41 22 476. The coupling comprises mating male and female connectors, which are closed off from the surrounding atmosphere by each a rubber membrane and sterilized. When the connectors should be interconnected, the rubber membranes are brought into contact with each other and the membrane of the female connector is exposed to a force so that it ruptures and allows the entering of the male connector. Then the rubber membrane of the male connector reaches a protrusion, which tensions the membrane until it ruptures, thereby exposing the female connector to the male connector for interconnection. This coupling is relatively well protected from contamination but does not reach the standards which the present invention aims to. Thus, normal air comprises thousands of bacteria per liter air, which are attached to particles "floating" in the air. Such particles always adhere to surfaces exposed to such air. Thus, any external surface is contaminated and must not come into contact with an area which is to be maintained sterile.

The connector according to DE 41 22 476 is also provided with an air relief channel including a sterile filter. Such a sterile filter is always a risk factor.

DISCLOSURE OF THE INVENTION

A first object of the present invention is to provide a sterile connector in which surfaces which has been exposed to external air, do not come into contact with areas that should be maintained sterile.

A second object of the invention is to provide a sterile connector that ensures that external air is never allowed into a sterile area.

A third object of the invention is to provide a sterile coupling in which a sterile filter is not required.

Thus, there is provided a sterile coupling comprising a male connector having a membrane device covering one end and the other end connected to a source of sterile fluid, and a female connector having a membrane device covering one end and the other end connected to a source of sterile fluid. According to the invention, each membrane device has a membrane surface, the exterior surface of which comprising an adhesive material and the interior surface of which facing the sterile area, so that the adhesive material when the two connectors are joined, form a bonded membrane surface. A rupture device is arranged to ruptures the bonded membrane surface inside said bonded membrane surface for forming said sterile coupling.

The membrane device may have a cup shape. The male and female connectors may each comprise a cylindrical body, forming a space there between during cooperation, said space accommodating the membrane devices after rupturing. The membrane surface may have a weakening line for guiding the rupture. Also, the membrane device of the male connector may be prestreched before use.

The adhesive layer may be covered by a tape before use, which is removed just before use. Also, the two connectors may have engagement means for interconnection thereof after the rupture of the membrane devices.

For avoiding entrapping air in the bonded area, one or both of the membrane devices may have grooves for letting out surplus air from the adhesive area before bonding.

Further objects, features and advantages of the invention will become apparent from the following detailed description of the invention with reference to the accompanying drawings which show several embodiments of the invention.

SHORT DESCRIPTION OF THE DRAWINGS

FIG. 4 is a cross-sectional view of a membrane device of the female connector.

FIG. 5 is a side view of the membrane device of FIG. 4 taken according to line V—V in FIG. 4.

FIG. 6 is a side view of a tape taken according to line VI—VI in FIG. 4.

FIG. 7 is a side view of the tape taken according to line VII—VII in FIG. 6.

DETAILED DESCRIPTION OF EMBODIMENTS

The major principle employed by the invention is that a sterile male connector is connected to a female connector in such a manner that no non-sterile areas can be reached by the gas or liquid that flows through the connected system, and no non-sterile air can come into contact with the gas or liquid being transferred.

This principle is employed by a female and a male connector having a central (inner) zone that is the transfer channel and where each zone is protected by a rubber membrane and where the central part of these membranes are connected to each other as described more closely below.

Furthermore, one of the connectors incorporates a device for rupturing the membranes as they are arranged in the sterile zone. As the two couplings are pushed together, the membranes will touch it and then the rupturing device will cause them to rupture.

The construction is such that at the moment of rupture, the membranes are stretched and the membranes will retract to the periphery leaving a free inner passage for the liquid to be transferred. To ensure that no non-sterile air can reach the passage, the membranes are designed not to rupture outside the connection zone. After coupling and punctuation, a sterile zone is created that does not incorporate any non-sterile surfaces nor any openings through which non-sterile air may intrude.

The sterile connection of membranes, which is a key for obtaining sterility, may be achieved by coating the membranes with a sticky material gluing the two membranes to each other. Alternatively, the same feature may be achieved through the fact that the membranes are fused together through the pressure that is created by the connecting process.

Another advantage of this invention is that the rubber membranes, when punctuated, retract into a ring-shaped space between the two couplings so dimensioned that the rubber, when it swells during contraction, fills this space and thereby connects the two couplings to each other so that no other locking device is needed. In this way, the rubber membranes are out of place from the fluid flow path.

The invention is described below with reference several embodiments thereof, which are shown only for elucidating the invention.

Figure 2:
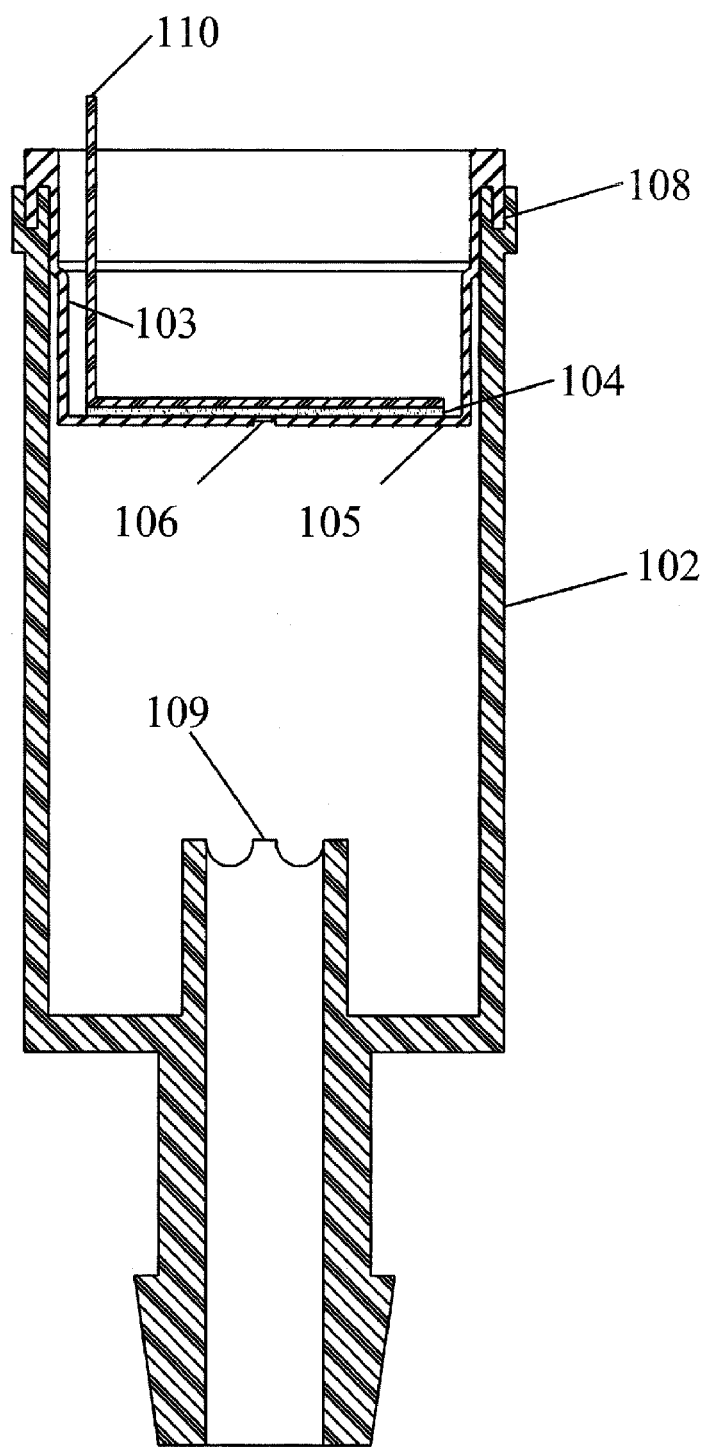
FIG. 2 is a cross-sectional view of the female connector of FIG. 1.

FIG. 2 discloses the female connector 10 according to the invention. The female connector has a substantially cylindrical housing 102 provided with a retention groove 108 at a first end thereof. The second end is connected to a vessel, bag, tube or other device, not shown.

In the groove 108 is inserted a female membrane device 103 to be further described below. The membrane device 103 completely closes the first end of the female connector.

Moreover, the female connector is provided with rupturing means 109 arranged a distance to the left of the membrane device as seen in FIG. 2. The female connector is sterilized, normally together with the bag or tube connected to the second end.

Figure 3:
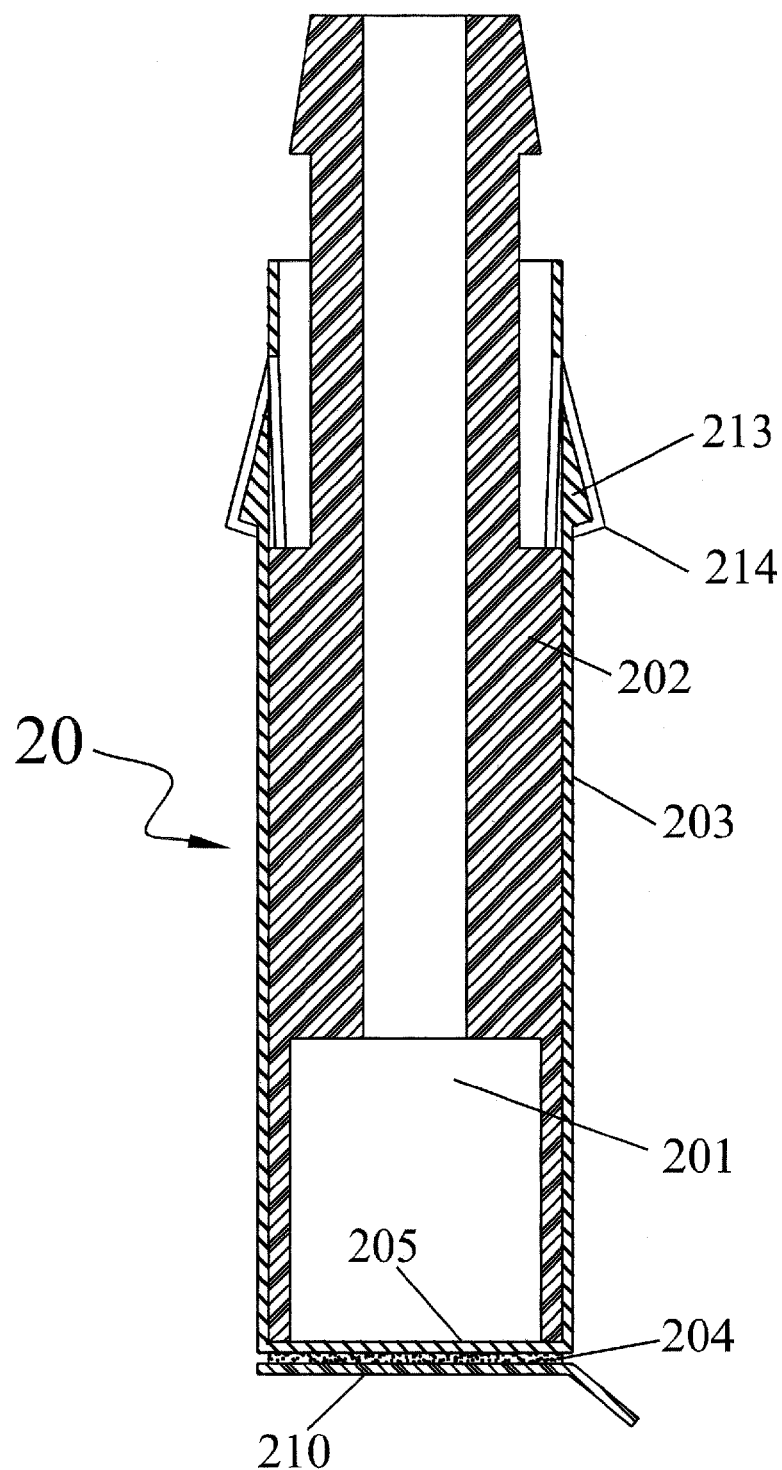
FIG. 3 is a cross-sectional view of the male connector of FIG. 1.

FIG. 3 discloses the male connector 20, which also is comprised of a substantially cylindrical housing 202, a first end of which being closed by a male membrane device 203, to be described in further detail below. The second end of the housing is connected to a vessel, bag, tube or other device, not shown. The male connector is sterilized, normally together with the bag or tube connected to the second end.

The female membrane device 103 is shown in further detail in FIGS. 4–7. The membrane device comprises a shoulder portion 107 intended to sealingly cooperate with the groove 108 of the female connector. Moreover, the membrane device comprises a substantially circular membrane 105 which covers substantially the complete cross-sectional area of the housing 102 and is offset somewhat to the left in FIG. 2 in relation to the first end. Thus, the membrane device has approximately a cup shape, with the outside of the cup facing the sterile area.

The interior, sterile surface of the membrane 105, to the left in FIGS. 2 and 4, is provided with a cross-shaped groove 106 or weakening portion, as is best shown in FIG. 5. The groove is intended for facilitating rupturing of the membrane as described below.

The exterior, non-sterile surface of the membrane is provided with an adhesive layer 104, covered by a protective tape 110, which is shown in more detail in FIGS. 6 and 7. The tape covers the adhesive layer until use, and maintains the stickiness of the adhesive. As shown in FIG. 7, the tape includes a flap extending out from the cup-shaped membrane device for removing the tape.

Figure 8:
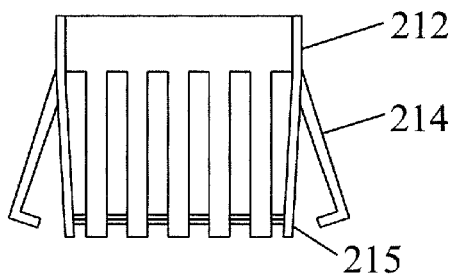
FIG. 8 is a cross-sectional view of a membrane device of the male connector.
Figure 9:
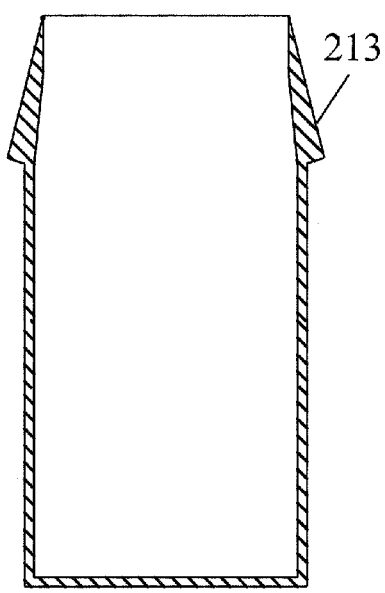
FIG. 9 is a cross-sectional view of a tensioning sleeve of the male connector.
Figure 10:
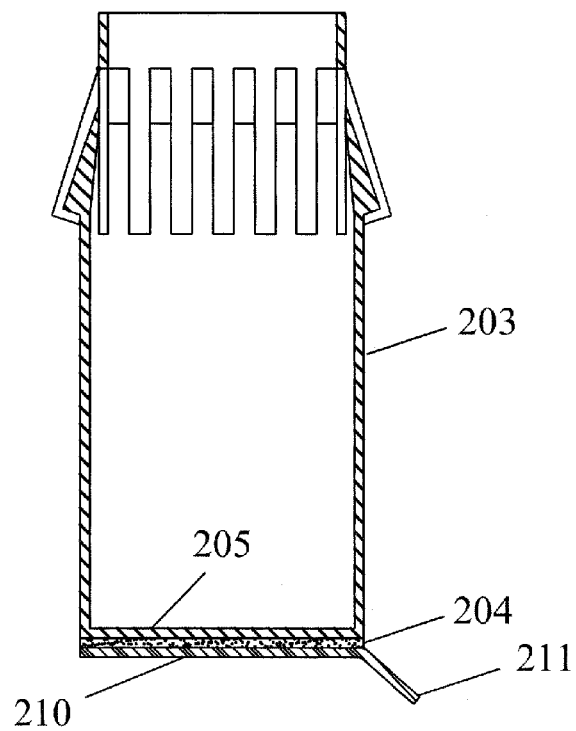
FIG. 10 is a cross-section view of the membrane device of FIG. 8 assembled with the tensioning sleeve of FIG. 9.

The male membrane device 203 is shown in further detail in FIGS. 8–10. The membrane device has a cup shape, in which the inside of the cup faces the sterile region. The flat bottom, circular surface of the cup comprises a membrane 205, which at the non-sterile exterior surface is covered with an adhesive layer 204, which is compatible with the adhesive layer 104 of the female membrane device. The adhesive layer is covered by a tape 210 arranged for maintaining the stickiness of the adhesive until use. The tape 210 has a flap 211 for easy removal of the tape at use.

The membrane device is intended for cooperation with a tensioning sleeve 212. Thus, the membrane device is provided with enlargement shoulder 213 at the right end in FIG. 8 for cooperation with hooks arranged at sleeve 212. Moreover, sleeve 212 is provided with a shoulder 215, which is the left end of the sleeve, in FIG. 9.

The membrane device 203 and the sleeve 212 are mounted together by inserting the enlargement shoulder 213 into engagement with the hooks 214, as shown in FIG. 10.

Finally, the assembled membrane device and sleeve are attached to the male connector as shown in FIG. 3, by passing the assembly over the first end of the male connector. The membrane device is made of an elastic material, so that the sleeve may be pushed to the right in FIG. 3 until the shoulder 215 of sleeve 212 cooperates with a ring-shaped groove 216 of the male connector. In this way, the membrane device is attached to the male connector and the elastic material thereof is stretched or tensioned. The complete assembly is attached to the tube of bag, and sterilized together therewith.

The sterile coupling is mounted in the following manner. The tapes 110 and 210 are removed by tearing in the flaps 111, 211 to expose the sticky surfaces of the membrane devices. Then, the first end (left end in FIG. 3) of the male connector is inserted into the cup-shaped membrane device of the female connector until the sticky surface 204 contacts the sticky surface 104, which then adheres to each other and form a bond.

Figure 1:
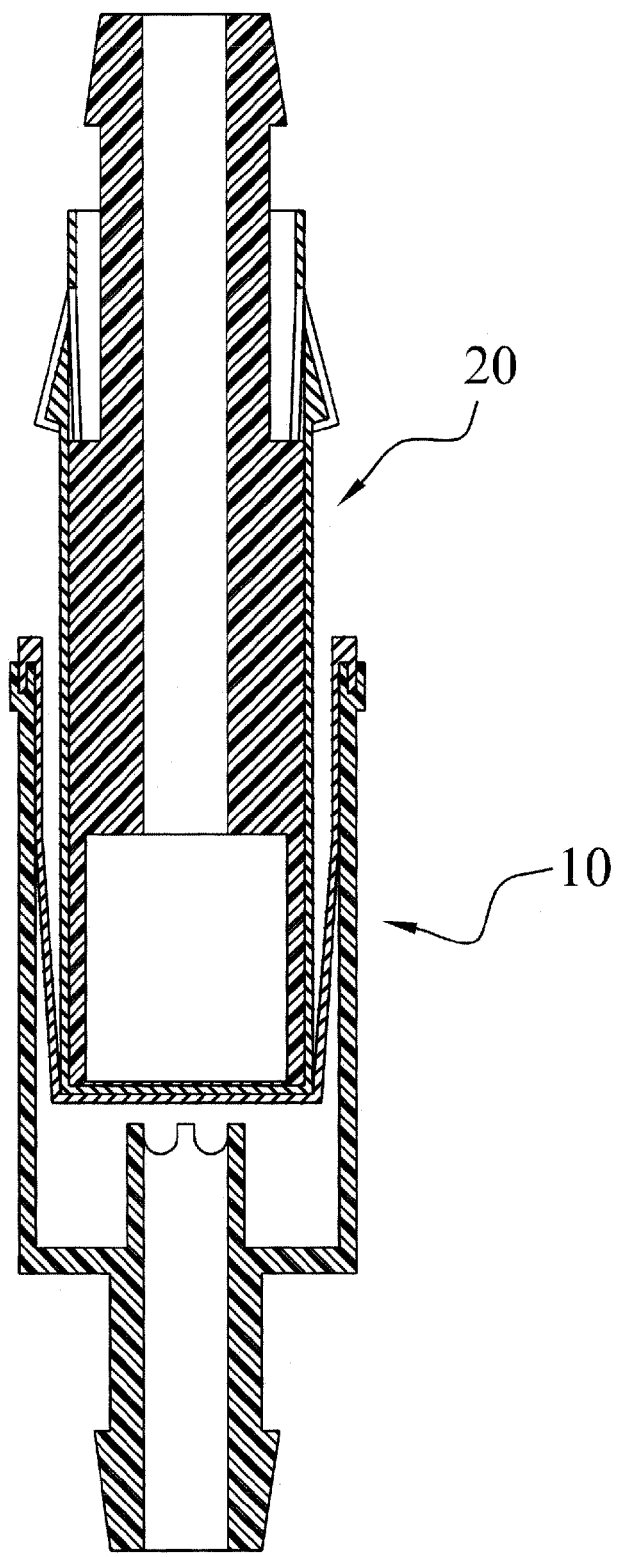
FIG. 1 is a cross-sectional view of a sterile coupling according to the invention, in which a female and a male connector are partially inserted into each other.

Then, the male connector is further inserted into the female connector as shown in FIG. 1, under tensioning of the female membrane device. By further insertion of the male connector, the bonded membranes 105, 104, 204, 205 reaches the rupturing means 109, which engages with the grooves of weakening lines 106 arranged in membrane 105. Then, the membrane ruptures according to lines 106 together with the bonded membrane 205. Since the membrane devices are now under heavy tension, they rapidly withdraw and pass into the free space between the cylindrical bodies of the connectors. Now, the flow path is open between the two connector elements.

Since the two membranes are bonded together, there is no risk that any surface that has been exposed to the surrounding atmosphere will face or contact the internal sterile area. Moreover, no external air can enter the sterile area, since the two membrane devices are bonded together and do not let in any surrounding air. Finally, no sterile filter means are required, since no air is moved. The only movement of air takes place when the male connector is inserted in the female connector, but that air is simply moved to the left in FIG. 1 into the tube system.

When the elastic membrane devices withdraw after rupture into the space between the cylindrical bodies, it expands slightly, thereby to fix the two connector bodies in relation to each other.

The membrane devices may be made of rubber material or any elastomeric material, such as Neoprene (tin) rubber. The thickness of the material may be around 0.1 mm.

The adhesive material may be a contact adhesive that adheres to each other as soon as contact is made. It may alternatively be a pressure activated adhesive, so that the bonding takes place more and more, when the male connector is inserted in the female connector under increased pressure.

The tape is preferably of a plastic material, which has a release layer, comprising for example silicon.

The connector parts are made of a medically compatible material such as PVC or ABS plastics. It may be transparent.

Figure 11:
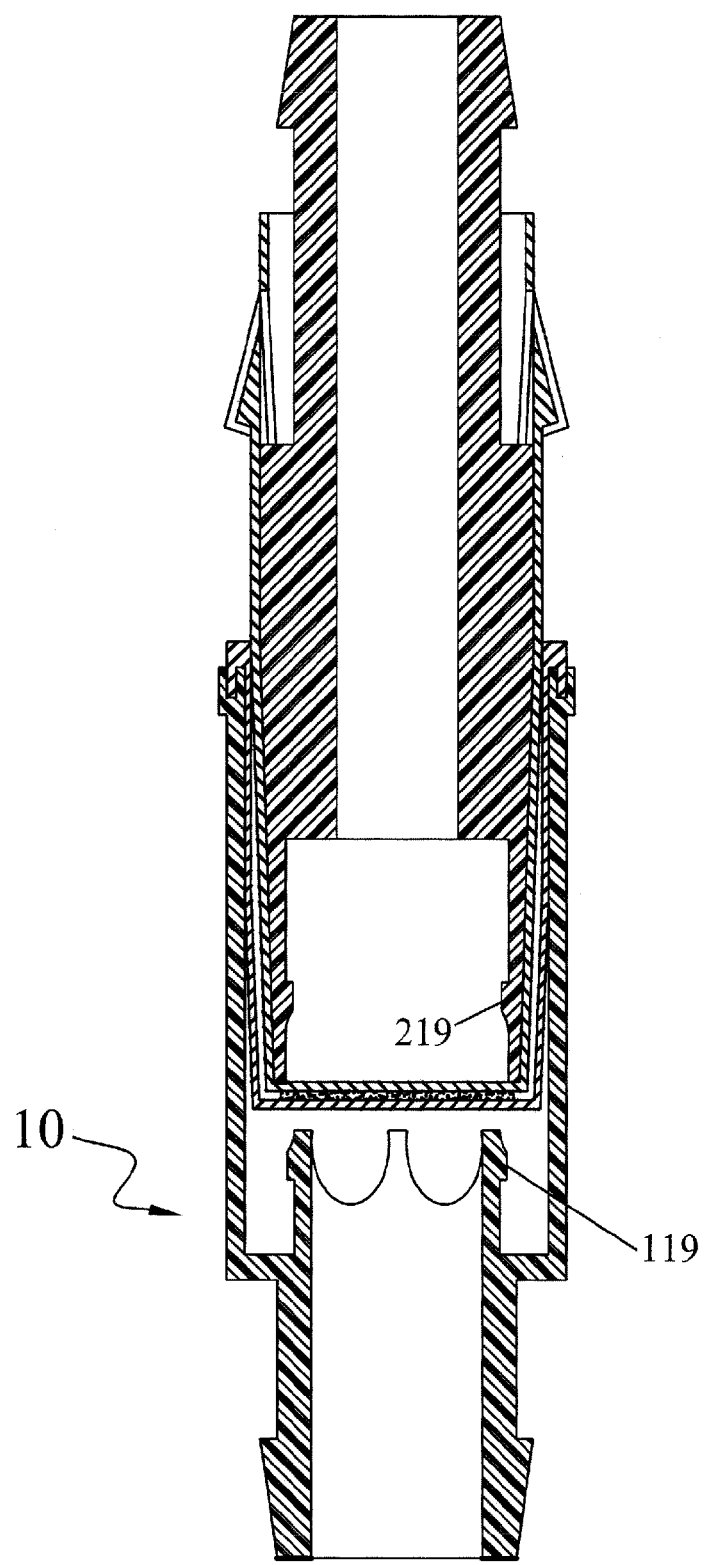
FIG. 11 is a cross-section view similar to FIG. 1 of an alternative sterile connector according to the invention.

A second embodiment of the invention is shown in FIG. 11. The difference is mainly that the two connectors are provided with positive engagement means 119 in the nature of shoulders and corresponding recess 219. After rupture of the membranes, the male connector is further inserted into the female connector until the shoulder 119 has passed into recess 219. In this manner, a closed fluid channel is formed. Thus, the adhesive, that may become exposed to the sterile area may not come into contact with the sterile fluid.

Figure 12:
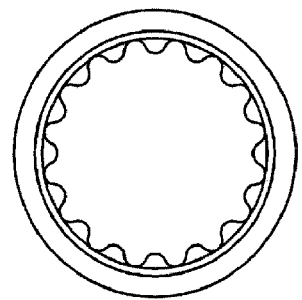
FIG. 12 is a plan view of a cup-shaped female membrane device provided with grooves.

No air should be entrapped between the two membranes as they are bonded, otherwise contaminated air may enter the sterile area. Thus, the female membrane device 103 may be provided with longitudinal grooves or foldings as indicated in FIG. 12, in the exterior surface. Any air can pass from the membrane 105 and in the grooves beyond the male body portion.

Figure 13:
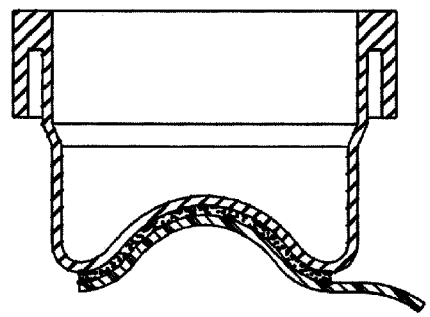
FIG. 13 is a cross-sectional view of a cup-shaped female membrane device having a doom-shaped bottom surface.

Another design for obtaining the same benefit is shown in FIG. 13. Here, the membrane 105 is dome-shaped in order to have a first contact point in the middle and then increase the contact surface progressively outwards. In this way, all air between the two membranes is effectively moved away.

Figure 14:
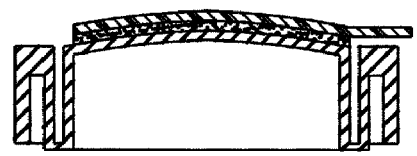
FIG. 14 is a cross-sectional view of a cup-shaped female membrane device having partially inverted bottom section.

It may be advantageous to arrange the membrane 104 closer to the first end, as shown in FIG. 14. Here, the longitudinal membrane portion is folded backwards, as clearly appears from the figure. Thus, the two membrane's sticky surfaces contact each other directly without any risk for air entrapment between the membranes.

Figure 15:
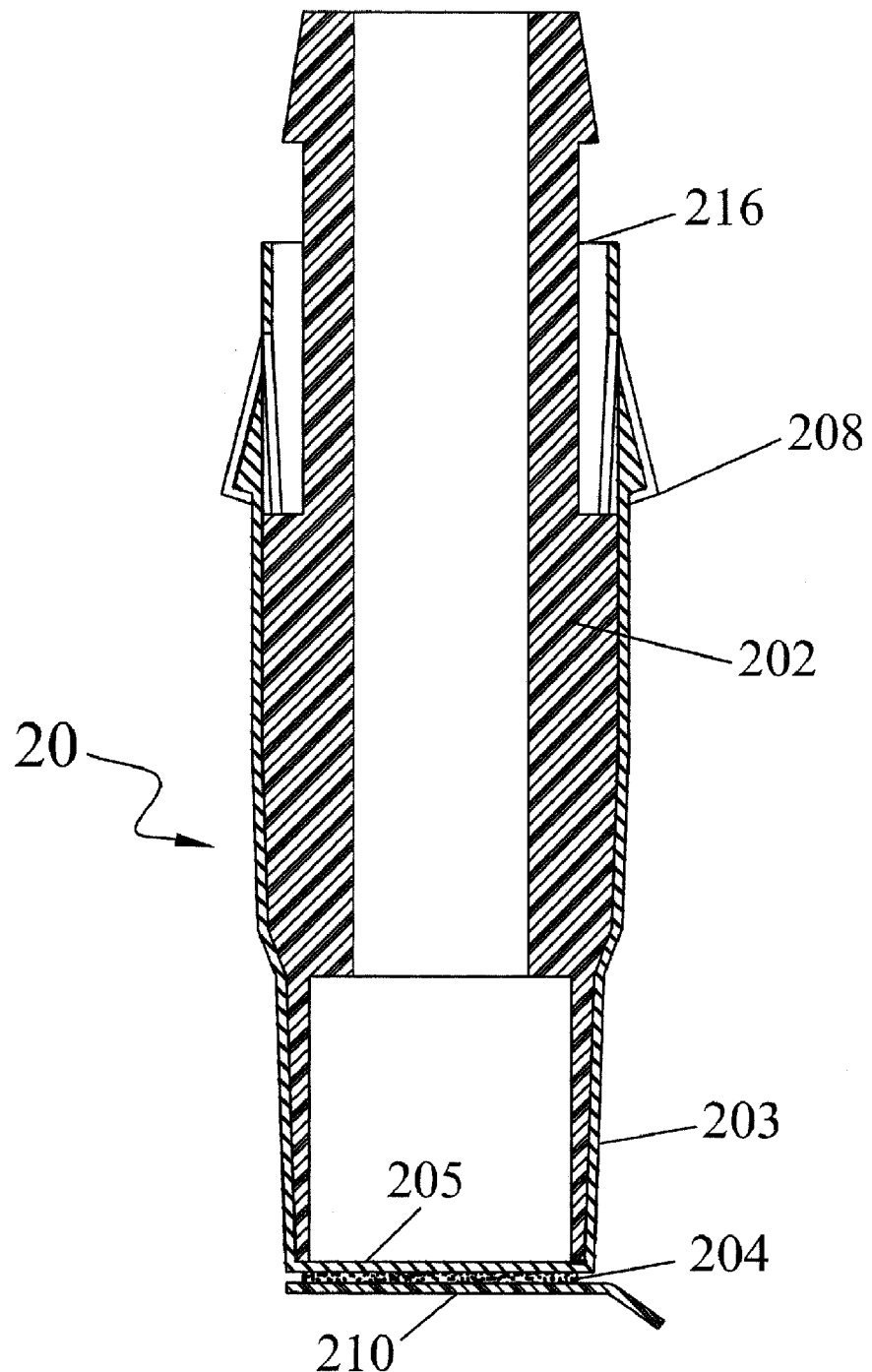
FIG. 15 is a cross-sectional view of the male connector having reduced first end section.

The same benefits may be obtained by arranging the male connector narrower at the first end, as shown in FIG. 15.

It is realized that the two membrane devices are bonded together over an area, and then a hole is generated through the two surfaces in the bonded area. Thus, the two membrane devices are interconnected so that no outside air may enter. It is essential that the hole does not extend outside the bonded area, which thus need to be large enough to fulfill its purpose.

One or both of the sticky rubber surfaces can be covered with an anti-bacterial agent such as cloridehexdrine as an extra precaution.

Hereinabove, the invention has been described with references to preferred embodiments with reference to the drawings. However, different combinations and modifications which occur to a skilled person reading the present specification are intended to be encompassed by the invention, which is only limited by the appended patent claims.

The invention claimed is:

1. A sterile coupling comprising a male connector having a first membrane device covering a first end and a second end adapted to be connected to a sterile region, said first membrane device being fixedly connected to said male connector adjacent said second end of said male connector and a female connector having a second membrane device covering a first end and a second end adapted to be connected to a sterile region, each membrane device having an exterior surface comprising an adhesive material and an interior surface facing a sterile area, so that the adhesive materials form a bonded membrane surface when the two connectors are joined, and a rupture device mounted within said female connector, which ruptures the bonded membrane surface inside said female connector for forming said sterile coupling.

2. The sterile coupling according to claim 1, wherein said second membrane device of said female connector is fixedly connected to said female connector adjacent said first end of said female connector and has a cup-shape extending into said female connector.

3. The sterile coupling according to claim 1, wherein said male and female connectors each comprises a cylindrical body, forming a space therebetween during cooperation, said space accommodating the membrane devices after rupturing and said membrane devices expanding in said space to fix said male and female connectors in relation to each other.

4. The sterile coupling according to claim 1, wherein said interior surface of said second membrane device of said female connector comprises a weakening line for guiding the rupture and wherein said rupture device comprises at least one prominence which engages said weakening line.

5. The sterile coupling according to claim 1, wherein the first membrane device of the male connector is pre-stretched before use.

6. The sterile coupling according to claim 1, wherein each said adhesive material is covered by a tape before use, which is removed just before use.

7. The sterile coupling according to claim 1, wherein an interior surface of said male connector comprises a shoulder and an exterior surface of said rupture device comprises a complementary shoulder for interconnection thereof after the rupture of said membrane devices.

8. The sterile coupling according to claim 2 characterized in that one or both of the membrane devices comprise grooves for letting out surplus air from an area of adhesive materials.

9. The sterile coupling according to claim 2, characterized in that said male and female connectors each comprises a cylindrical body, forming a space therebetween during cooperation, said space accommodating the membrane devices after rupturing and said membrane devices expanding in said space to fix said male and female connectors in relation to each other.

10. The sterile coupling according to claim 2, wherein said interior surface of said second membrane device of said female connector comprises a weakening line for guiding the rupture and wherein said rupture device comprises at least one prominence which engages said weakening line.

11. The sterile coupling according to claim 3, wherein said interior surface of said second membrane device of said female connector comprises a weakening line for guiding the rupture and wherein said rupture device comprises at least one prominence which engages said weakening line.

12. The sterile coupling according to claim 2, wherein the first membrane device of the male connector is pre-stretched before use.

13. The sterile coupling according to claim 3, wherein the first membrane device of the male connector is pre-stretched before use.

14. The sterile coupling according to claim 4, wherein the first membrane device of the male connector is pre-stretched before use.

15. The sterile coupling according to claim 2, wherein each said adhesive material is covered by a tape before use, which is removed just before use and wherein said tape in said cup-shaped membrane device has a flap extending out of said cup-shaped membrane device.

16. The sterile coupling according to claim 3, wherein each said adhesive material is covered by a tape before use, which is removed just before use.

17. The sterile coupling according to claim 4, wherein each said adhesive material is covered by a tape before use, which is removed just before use.

18. The sterile coupling according to claim 5, wherein each said adhesive material is covered by a tape before use, which is removed just before use.

19. The sterile coupling according to claim 2, wherein an interior surface of said male connector comprises a shoulder and an exterior surface of said rupture device comprises a complementary shoulder for interconnection thereof after the rupture of said membrane devices.

20. The sterile coupling according to claim 3, wherein an interior surface of said male connector comprises a shoulder and an exterior surface of said rupture device comprises a complementary shoulder for interconnection thereof after the rupture of said membrane devices.

21. The sterile coupling according to claim 1 wherein said first membrane device comprises an enlargement shoulder for securing said first membrane device under tension to said male connector.

22. The sterile coupling according to claim 21 further comprising a tensioning sleeve adapted to engage said enlargement shoulder and said male connector.

23. The sterile coupling according to claim 22 wherein said tensioning sleeve further comprises a plurality of hooks for engaging said enlargement shoulder and a shoulder adapted to engage a groove in said male connector whereby said first membrane device is stretched over said male connector.

24. The sterile coupling according to claim 3 wherein said male connector is tapered towards said first end thereof.

25. The sterile coupling according to claim 2 wherein said second membrane device further comprises a shoulder adapted to engage said first end of said female connector.

26. The sterile coupling according to claim 25 wherein said first end of said female connector further comprises a groove that receives said shoulder of said second membrane.

27. The sterile coupling according to claim 1 wherein said second membrane device is secured to said female connector at said first end thereof, and a longitudinal portion of said second membrane device extends into said female connector along an interior wall of said female connector, and said longitudinal portion is folded back on itself such that said adhesive material of said second membrane device is adjacent said first end of said female connector.

28. The sterile coupling according to claim 2 wherein said adhesive material of said second membrane is domed towards said first end of said female connector.

* * * * *